United States Patent
Lange et al.

(10) Patent No.: US 10,624,832 B2
(45) Date of Patent: *Apr. 21, 2020

(54) PRODUCT AND METHOD FOR THE TEMPORARY SHAPING OF KERATIN-CONTAINING FIBERS

(71) Applicant: Henkel AG & Co. KGaA, Duesseldorf (DE)

(72) Inventors: Julia Bibiane Lange, Bad Bramstedt (DE); Anna Puls, Winsen (DE); Cyrielle Martinez, Hamburg (DE); Bernd Richters, Hamburg (DE)

(73) Assignee: Henkel AG & Co. KGaA, Duesseldorf (DE)

(*) Notice: Subject to any disclaimer, the term of this patent is extended or adjusted under 35 U.S.C. 154(b) by 50 days.

This patent is subject to a terminal disclaimer.

(21) Appl. No.: 15/556,624

(22) PCT Filed: Jan. 26, 2016

(86) PCT No.: PCT/EP2016/051565
§ 371 (c)(1),
(2) Date: Sep. 8, 2017

(87) PCT Pub. No.: WO2016/142091
PCT Pub. Date: Sep. 15, 2016

(65) Prior Publication Data
US 2018/0055759 A1  Mar. 1, 2018

(30) Foreign Application Priority Data
Mar. 9, 2015  (DE) .................. 10 2015 204 153

(51) Int. Cl.
*A61K 8/81* (2006.01)
*A61K 8/41* (2006.01)
*A61Q 5/06* (2006.01)

(52) U.S. Cl.
CPC ............. *A61K 8/8182* (2013.01); *A61K 8/41* (2013.01); *A61K 8/8147* (2013.01); *A61K 8/8152* (2013.01); *A61Q 5/06* (2013.01); *A61K 2800/594* (2013.01)

(58) Field of Classification Search
CPC .. A61K 2800/594; A61K 8/41; A61K 8/8147; A61K 8/8152; A61K 8/8182; A61Q 5/06
See application file for complete search history.

(56) References Cited

U.S. PATENT DOCUMENTS

| 6,482,390 | B1 | 11/2002 | Hiscocks et al. | |
| 6,482,394 | B1* | 11/2002 | Schehlmann | A61K 8/046 424/47 |
| 2005/0251600 | A1 | 11/2005 | Chen | |
| 2006/0251600 | A1 | 11/2006 | Tamareselvy et al. | |
| 2014/0093467 | A1* | 4/2014 | Knappe | A61K 8/8152 424/70.15 |
| 2015/0017113 | A1* | 1/2015 | Metten | A61Q 5/06 424/70.15 |

FOREIGN PATENT DOCUMENTS

| EP | 1878423 A2 | 1/2008 | |
| WO | WO 2012/168311 | * 12/2012 | ............... A61K 8/73 |
| WO | WO 2013/091995 | * 6/2013 | |
| WO | 2015095870 A1 | 6/2015 | |

OTHER PUBLICATIONS http://ashlandstylebook.com/wp-content/uploads/2015/01/ASH PC7934_AquaStyle_SH_100_Brochure.pdf Mar. 20, 2014). (Year: 2014).*
EPO, International Search Report and Written Opinion issued in International Application No. PCT/EP2016/051565, dated Apr. 20, 2016.
Ashland, "Ashland Brings Performance and Style to Crystal Clear Gel with AquaStyle: New, Higlhy Functional Polymer for Hair Styling Formulations Offers Consumer-Perceivable Styling Benefits That Stand Up to High Humidity Conditions", Apr. 1, 2014.
Mintel, "Styling Mousse", www.gnpd.com, 2014.
Mintel, "Ultra Power Styling Gel", www.gnpd.com, Mar. 2014.
Mintel, "Full Form Mousse", www.gnpd.com, Nov. 2013.
Mintel, "Curl Enhancing Styling Foam", www.gnpd.com, Jun. 2014.
Mintel, "Extreme max Gel for Men", www.gnpd.com, Sep. 2014.
Mintel, "Wellaflex Mousse", www.gnpd.com, Jul. 2004.

* cited by examiner

*Primary Examiner* — Anna R Falkowitz
(74) *Attorney, Agent, or Firm* — Lorenz & Kopf, LLP

(57) ABSTRACT

The disclosure relates to a cosmetic composition for the temporary shaping of hair, containing a combination of two specific copolymers, a polymeric quaternary ammonium compound from the group of the vinylpyrrolidone copolymers and an anionic acrylate copolymer. The cosmetic composition provides an extremely good moisture resistance.

8 Claims, No Drawings

PRODUCT AND METHOD FOR THE TEMPORARY SHAPING OF KERATIN-CONTAINING FIBERS

CROSS-REFERENCE TO RELATED APPLICATION

This application is a U.S. National-Stage entry under 35 U.S.C. § 371 based on International Application No. PCT/EP2016/051565, filed Jan. 26, 2016 which was published under PCT Article 21(2) and which claims priority to German Application No. 10 2015 204 153.0, filed Mar. 9, 2015, which are all hereby incorporated in their entirety by reference.

TECHNICAL FIELD

The present disclosure relates to a cosmetic composition for setting hair and/or for the temporary reshaping of keratinous fibres, particularly human hair, wherein the composition contains a combination of a cationic and an anionic polymer.

BACKGROUND

The temporary design of hairstyles to last for prolonged periods of up to several days typically requires the application of setting agents. Therefore, hair treatment products which are used to create temporary hairstyles are very important. Corresponding agents for temporary reshaping typically contain synthetic polymers and/or waxes as the setting agent. Products to support the temporary reshaping of keratinous fibres may be packaged in the form of hairspray, hair wax, hair gel, hair mousse for example.

The most important property of an agent for temporary shaping of hair, also referred to hereinafter as styling agents, is that it confers the strongest possible hold on the treated fibres in the newly modelled form—i.e. a shape imposed on the hair. This is also called a strong hairstyle hold or a high degree of hold of the styling agent. Styling hold is essentially determined by the type and amount of active setting ingredients used, although the other components of the styling agent may also have some effect.

Besides a high degree of hold, styling agents must also fulfil a number of other requirements. These can be classified roughly according to the properties of the respective formulation, for example properties of the foam, gel or sprayed aerosol, and properties relating to the handling of the styling agent, wherein the properties on the hair acquire particular importance. These include particularly moisture resistance, low stickiness (tack) and a balanced conditioning effect. Moreover, a styling agent should be usable for the broadest possible range of hair types and gentle on the hair and skin.

In order to satisfy these various requirements, many synthetic polymers for use in styling products have already been developed as setting agents. The polymers can be subdivided into cationic, anionic, nonionic and amphoteric setting polymers. Ideally, when applied to the hair these polymers create a polymer film which on the one hand lends a firm hold to the hairstyle but at the same time is also flexible enough not to break under stress. If the polymer film is too brittle, leading to the formation of so-called film scales, that is to say residues that are shed with movement of the hair and evoke the impression that the user of the respective styling agent has dandruff. Similar problems are encountered when waxes are used as the setting agent in styling agents. If the styling agent is a gel or paste, the polymers should also possess thickening properties.

Thus, German patent application DE 10 2011 089 170 A1 describes hair cosmetics for temporary hair reshaping, which besides other ingredients also contain at least one polymeric quaternary ammonium compound from the group of vinylpyrrolidone copolymers.

Hydrophobically modified acrylate copolymers (INCI: Acrylates Copolymer (and) Water) that act essentially as thickeners are also available commercially. The datasheet Aquastyle® SH-100 polymer (Ashland Inc.) describes such an acrylate copolymer and its use in combination with carbomers. Its suitability for use in crystal clear hair gels, good initial stiffness, moisture resistance and long-term effectiveness are described.

One of the objects as contemplated herein was to provide further suitable polymer combinations which are exemplified by good film-forming and/or setting properties, have a very high degree of hold without sacrificing flexibility and good moisture resistance—particularly to sweat and water—and are also suitable for producing consistently viscous and consistently transparent cosmetic compositions. In particular, the styling agents currently available are still capable of improvement in the sense that a good combination of stiffness and long-term maintenance (high humidity curl retention) is not always adequately assured. It is therefore an object as contemplated herein to provide styling agents of such kind which in addition to the aforementioned properties, in particular deliver both good stiffness and good long-term stability.

BRIEF SUMMARY

A cosmetic composition for the temporary reshaping of keratinous fibres is provided herein. The cosmetic composition includes at least one polymeric quaternary ammonium compound from the group of vinylpyrrolidone copolymers. The cosmetic composition further includes at least one anionic acrylate copolymer (b). The at least one anionic acrylate copolymer (b) is composed of at least the following monomer units: (b1) at least one (meth)acrylic acid unit, (b2) at least one (meth)acrylic acid ethyl ester unit, and (b3) at least one (meth)acrylic acid ester unit. The at least one (meth)acrylic acid ester unit (b3) is different from (meth)acrylic acid ethyl ester unit (b2) and includes a hydrophobic group as the ester group.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

This was achieved as contemplated herein with a combination of two specific polymers.

The present disclosure provides the following:
1. A cosmetic composition for the temporary reshaping of keratinous fibres, comprising:
(a) at least one polymeric quaternary ammonium compound from the group of vinylpyrrolidone copolymers and
(b) at least one anionic acrylate copolymer (b) which is composed of at least the following monomer units:
(b1) at least one (meth)acrylic acid unit
(b2) at least one (meth)acrylic acid ethyl ester unit (b3) at least one (meth)acrylic acid ester unit that is different from (meth)acrylic acid ethyl ester unit (b2) and contains a hydrophobic group as the ester group.

2. A cosmetic composition according to item 1, wherein the at least one vinylpyrrolidone copolymer (a) is constructed from at least the following monomer units:
(a1) vinylpyrrolidone
(a2) methacrylamidopropyltrimethylammonium chloride.

3. A cosmetic composition according to any of the preceding points, wherein the at least one vinylpyrrolidone copolymer (a) is a copolymer of methacrylamidopropyltrimethylammonium chloride (MAPTAC) with vinyl pyrrolidone, which contains from about 40 to about 95 mol %, preferably 42.5 to 90 mol %, more preferably from about 45 to about 85 mol % and in particular from about 50 to about 80 mol % vinylpyrrolidone.

4. A cosmetic composition according to any of the preceding points, wherein the composition contains a percentage of vinylpyrrolidone copolymer (a) in a proportion of from about 1.0 to about 5.0 wt %, preferably from about 1.5 to about 4.0 wt % and in particular from about 2.0 wt % to about 3.0 relative to the total weight of the cosmetic composition.

5. A cosmetic composition according to any of the preceding points, wherein the anionic acrylate copolymer (b) contains methacrylic acid as monomer unit (b1) and ethyl acrylate as monomer unit (b2).

6. A cosmetic composition according to any of the preceding points, wherein the anionic acrylate copolymer (b) has a (meth)acrylic acid alkyl ester as monomer unit (b3).

7. A cosmetic composition according to any of the preceding points, wherein the composition contains the anionic acrylate copolymer (b) in a proportion of from about 0.1 to about 5.0 wt %, preferably from about 1.0 to about 4.0 wt % and in particular from about 1.5 to about 3.0 wt % relative to the total weight of the cosmetic composition.

8. A cosmetic composition according to any of the preceding points, wherein the anionic acrylate copolymer (b) has a viscosity from about 60,000 to about 120,000 cps with a solid content of 2 wt % in an aqueous neutralized solution at 25° C.

9. A cosmetic composition according to any of the preceding points, wherein the vinylpyrrolidone copolymer (a) is a copolymer with INCI name Polyquaternium-28, in particular Gafquat® HS 100 (ISP).

10. A cosmetic composition according to any of the preceding points, wherein the anionic acrylate copolymer (b) is a copolymer with INCI name Acrylates Copolymer (and) Water, particularly Aquastyle SH-100 (Ashland Inc.).

11. A cosmetic composition according to any of the preceding points, wherein the vinylpyrrolidone copolymer (a) is a copolymer with INCI name Polyquaternium-28 and the anionic acrylate copolymer (b) is a copolymer with INCI name Acrylates Copolymer (and) Water.

12. A cosmetic composition according to any of the preceding points, wherein the at vinylpyrrolidone copolymer (a) is Gafquat® HS 100 (ISP) and the anionic acrylate copolymer (b) is Aquastyle® SH 100 (Ashland Inc.).

13. A cosmetic composition according to any of the preceding points, which contains:
from about 1.0 to about 5.0 wt % of the vinylpyrrolidone copolymer (a), and
from about 0.1 to about 15 wt % of the anionic acrylate copolymer (b)
relative to the total weight of the cosmetic composition.

14. A cosmetic composition according to any of the preceding points, containing:
from about 2.0 to about 3.0 wt % of the vinylpyrrolidone copolymer (a), and
from about 5.0 to about 10 wt % of the anionic acrylate copolymer (b)
relative to the total weight of the cosmetic composition.

15. A cosmetic composition according to any of the preceding points, wherein the composition further contains at least one polymer (c) that differs from copolymers (a) and (b), in particular an anionic or nonionic polymer (c).

16. A cosmetic composition according to any of the preceding points, characterised in that it further contains
c) from about 1.0 to about 10 wt % polyvinylpyrrolidone, and/or vinylpyrrolidone/vinylacetate copolymer, preferably polyvinyl pyrrolidone
relative to the total weight thereof.

17. A cosmetic composition according to item 16, characterised in that the percentage by weight of polyvinylpyrrolidone and/or vinylpyrrolidone/vinylacetate copolymer c) of the total weight of the cosmetic composition is from about 2.0 to about 8.5 wt %, preferably from about 3.0 to about 7.0 wt %.

18. A cosmetic composition according to any of the preceding points, wherein the composition contains water in a percentage from about 50 to about 95 wt %, preferably between about 60 and about 90 wt % and in particular between about 65 and about 85 wt % relative to the total weight of the cosmetic composition.

19. A cosmetic composition according to any of the preceding points, wherein the composition is provided as a hair gel, hair spray, hair foam, or hair wax, in particular a hair gel.

20. Use of a cosmetic composition according to any of items 1 to 19 for the temporary reshaping of keratinous fibres.

21. Use of a cosmetic composition according to any one of items 1 to 19 to improve the moisture resistance temporarily deformed keratinous fibres.

22. A method for the temporary shaping of keratinous fibres, particularly human hair, in which the cosmetic composition according to any one of items 1 to 19 is applied to keratinous fibres.

Surprisingly, it was found in the context as contemplated herein that improved moisture resistance of styling products can be obtained by combining two ingredients that are known per se and are already used in styling products. Other commonly requested properties of styling products such as long-term hold, stiffness and low tack remained unchanged. Such a good combination of properties was not expected even with knowledge of the individual components and was surprising. It was found experimentally that combining the two components produced a strong super-additive, i.e. synergistic effect with respect to moisture resistance, which manifested itself in the high humidity curl retention (HHRC) test.

For the purposes as contemplated herein, the term keratinous fibres comprises furs, wool and feathers, but particularly human hair.

The essential components of the cosmetic composition as contemplated herein are the vinylpyrrolidone copolymer (a) and the anionic acrylate copolymer (b) which is different from copolymer (a).

The cosmetic compositions contain, a polymeric quaternary ammonium compound from the group of vinyl pyrrolidone copolymers (a) as the first essential component. Cosmetic compositions in which the copolymer a) constitutes a percentage by weight from about 1.0 to about 5.0 wt %, preferably from about 1.5 to about 4.0 wt % and particularly from about 2.0 to about 3.0 wt % relative to the total weight of the composition are distinguished by particularly advantageous cosmetic properties.

Suitable copolymers (a) are for example
quaternised vinylpyrrolidone/dimethylaminoethylmethacrylate copolymer (INCI name Polyquatemium-11), for example the copolymers with tradenames Gafquat® 755N and Gafquat® 734 (Gaf Co., USA) and Luviquat® PQ 11 PN (BASF);
vinylpyrrolidone/imidazolimine methochloride copolymer (INCI name Polyquatemium-16), for example the copolymer Luviquat® HM 552 (BASF);
vinylpyrrolidone/methacrylamidopropyltrimethylammonium copolymer (INCI name Polyquatemium-28), for example the copolymer Gafquat® HS 100 (ISP);
methylvinylimidazolium chloride/vinylpyrrolidone copolymers (INCI name Polyquatemium-44), for example Luviquat® UltraCare (BASF);
quaternised vinylpyrrolidone/vinylcaprolactam/vinylimidazole copolymer (INCI name Polyquatemium-46), for example Luviquat® Hold (BASF);
quaternised vinylpyrrolidone/vinylcaprolactam/vinyl imidazole/quaternised vinylimidazole copolymer (INCI name Polyquaternium-68), for example Luviquat® Supreme (BASF).

The inventive products particularly preferably comprise at least one copolymer (a) selected from
b1) copolymers of vinylpyrrolidone with methacrylamidopropyltrimethylammonium chloride (MAPTAC) and/or
b2) copolymers of vinylpyrrolidone with dimethylaminoethylmethacrylate and/or
b3) copolymers of vinylpyrrolidone with dimethylaminopropylmethacrylamide and alkyldimethylpropyl methacrylamidoammonium salts.

A particularly suitable copolymer (a) is obtained by reacting vinylpyrrolidone with methacrylamidopropyltrimethylammonium chloride.

These copolymers of vinylpyrrolidone with methacrylamidopropyltrimethylammonium chloride (MAPTAC) can be described with the general formula

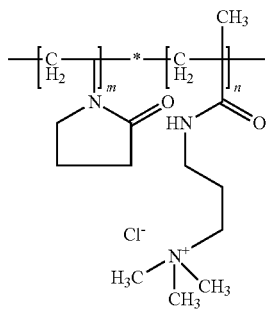

wherein the indices m and n vary according to the molecular weight of the polymer and are not intended to mean that these are block copolymers. Rather, structural units can be randomly distributed in the molecule.

Particularly preferred cosmetic products are exemplified in that they contain copolymers of methacrylamidopropyltrimethylammonium chloride (MAPTAC) with from about 40 to about 95 mol %, preferably from about 42.5 to about 90 mol %, more preferably 45 to 85 mol % and particularly from about 50 to about 80 mol % vinylpyrrolidone as vinylpyrrolidone copolymer (a).

Particularly preferred cosmetic products are further exemplified in that the copolymers (a) have molecular masses from about 10 to about 1000 kDa, preferably from about 25 to about 900 kDa, more preferably from about 50 to about 800 kDa and particularly from about 100 to about 750 kDa.

A particularly preferred copolymer (a) is designated Polyquaternium-28 according to INCI nomenclature. Such a polymer is marketed for example by ISP with trade name Gafquat® HS-100 (CAS Number: 131954-48-8).

The cosmetic compositions as contemplated herein contain an anionic acrylate copolymer (b) as the second essential ingredient.

The anionic acrylate copolymer (b) is constructed from at least the following monomer units: at least one (meth)acrylic acid unit (b1), at least one (meth)acrylic acid ethyl ester unit (b2) and at least one (meth)acrylic acid ester unit (b3) which is different from (meth)acrylic acid ethyl ester unit (b2) and contains a hydrophobic group as the ester group.

As contemplated herein, copolymer (b) may be constructed from other monomer units. However, according to a preferred embodiment as contemplated herein, copolymer (b) consists only of said units (b1), (b2) and (b3), i.e. it consists entirely of monomer units derived from these units.

The at least one (meth)acrylic acid unit (b1) may be a methacrylic acid unit or an acrylic acid unit, wherein a methacrylic acid unit is preferred.

The at least one (meth)acrylic acid ethyl ester unit (b2) may be a methacrylic acid ethyl ester unit or an acrylic acid ethyl ester unit, wherein an acrylic acid ethyl ester unit is preferred.

As contemplated herein the at least one (meth)acrylic acid ester unit (b3) may be a (meth)acrylic acid alkyl ester unit. The alkyl group in the (meth)acrylic acid alkyl ester unit serves to control the hydrophobicity of the copolymer. The alkyl group is preferably a linear or branched alkyl group having 2 to 30 carbon atoms, more preferably 3 to 12 carbon atoms. As contemplated herein the hydrophobic group may also be another hydrophobic group which is not an alkyl group, e.g. an aromatic hydrocarbon ester group. An example of such may be a substituted or unsubstituted phenyl ester group or a substituted or unsubstituted alkylene phenyl ester group, for example a benzyl ester group.

The viscosity of the anionic acrylate copolymer (b) used in the cosmetic composition with a solid content of 2 wt % and neutralized solution at 25° C. is preferably not more than about 60,000 to about 120,000 cPs.

Suitable anionic acrylate copolymers (b) are available commercially with the INCI name Acrylates Copolymer (and) Water. Most preferable is the anionic acrylic copolymer (b) Aquastyle® SH-100 polymer from Ashland, Inc. Tin the commercially available form, this has a solid content of from about 28 to about 32 wt % and a pH from about 2.1 to about 4.0.

The cosmetic composition as contemplated herein contains the vinylpyrrolidone copolymer (a) and acrylate copolymer (b) in quantities customary and suitable for styling agents, which may be adjusted for particular applications and packaging formats.

The composition as contemplated herein may contain the vinylpyrrolidone copolymer (a) for example in a quantity from about 1.0 to about 5.0 wt % relative to the total weight of the composition. Preferred are percentages of vinylpyrrolidone copolymer (a) from about 1.5 to about 4.0 wt % and particularly from about 2.0 to about 3.0 wt %, expressing in each case the solid content of active substance in the cosmetic composition.

The cosmetic composition contains the acrylate copolymer (b) e.g. in a quantity from about 0.1 to about 5.0 wt %, preferably from about 1.0 to about 4.0 wt %, more preferably from about 1.5 to about 3.0 wt % relative to the total weight of the cosmetic composition, expressing in each case the solid content of active substance in the cosmetic composition.

In addition to the advantages outlined in the preceding text, the cosmetic compositions as contemplated herein are also differentiated from alternative cosmetic products particularly by the improved long-term hold they provide. A weight ratio between polymers a) and b) in the cosmetic from about 5:1 to about 1:5, preferably from about 3:1 to about 1:3 and particularly from about 2:1 to about 1:2 has proven to be particularly advantageous for the cosmetic properties of the products as contemplated herein.

In a particularly preferred embodiment as contemplated herein, the cosmetic composition contains the copolymer which is available commercially under the name Gafquat® HS 100 as the vinylpyrrolidone copolymer (a) and the copolymer which is available commercially under the name Aquastyle® SH-100 as the anionic acrylate copolymer (b). In this combination, particularly good results were obtained with respect to a combination of stiffness and long-term hold. This polymer combination is particularly advantageously supplied in gel form in styling products.

Other generally required properties of styling products, such as moisture resistance and low stickiness are also achieved particularly with this combination, particularly when in a packaging format as hair gel.

Copolymers (a) and (b) are preferably used in the cosmetic composition in partially neutralized or neutralized form. Preferably at least one alkanolamine is used as the neutralizer. The alkanolamines usable as alkalizing agents as contemplated herein are preferably selected from primary amines with a $C_2$-$C_6$ alkyl base body which supports at least one hydroxyl group. Particularly preferred alkanolamines are selected from the group formed from 2-amino-1-ethanol (monoethanolamine), tris (2-hydroxyethyl) amine (triethanolamine), 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methyl propane-1-ol, 1-amino-2-methylpropan-2-ol, 3-amino-1,2-diol, 2-amino-2-methyl propan-1,3-diol. Very particularly preferred alkanolamines as contemplated herein are selected from the group 2-amino-1-ethanol, 2-amino-2-methyl propanol and 2-amino-2-methyl-propane-1,3-diol. Of these, 2-amino-2-methylpropanol has been found to be a particularly suitable neutralizing agent. Therefore, preferred cosmetic products as contemplated herein contain 2-amino-2-methylpropanol. 2-amino-2-methylpropanol is preferably used in the inventive products in an amount not exceeding the amount necessary to neutralize the acrylate copolymers (a) and (b). The quantities of 2-amino-2-methylpropanol used are preferably equivalent to from about 80 to 100%, particularly preferably from about 90 to 100%, and particularly from about 95 to 100% of the quantity required for complete neutralization of the acrylate copolymers (a) and (b). In a preferred embodiment, the proportion by weight of 2-amino-2-methylpropanol of the total weight of the cosmetic agent is from about 0.05 to about 7.0 wt %, preferably from about 0.1 to about 5.0 wt % and particularly from about 0.1 to about 3.0 wt %.

In summary, a preferred cosmetic composition for the temporary reshaping of keratinous fibres contains relative to the total weight thereof:

(a) from about 0.1 to about 5.0 of at least one polymeric quaternary ammonium compound from the group of vinylpyrrolidone copolymers, constructed from at least the following monomer units:
(a1) vinylpyrrolidone
(a2) methacrylamidopropyltrimethylammonium chloride, and
(b) from about 0.1 to about 5.0 of at least one anionic acrylate copolymer (b) constructed from at least the following monomer units:
(b1) at least one methacrylic acid unit
(b2) at least one acrylic acid ethyl ester unit
(b3) at least one methacrylic acid ester unit that is different from acrylic acid ethyl ester unit (b2) and contains a hydrophobic group as the ester group.

The cosmetic composition as contemplated herein preferably contains one or more further, component(s) to function as thickening or gelling agents, which is/are different from copolymers (a) and (b) and also support film formation. Examples of such are cationic, anionic, nonionic or amphoteric polymers. The proportion by weight of this additional component in the total weight of the cosmetic composition may be relatively low due to the presence of components (a) and (b) and is for example from about 0.02 to about 3 wt %, preferably from about 0.05 to about 1.5 wt %, more preferably from about 0.2 to about 0.8 wt %.

Examples are acrylamide/ammonium acrylate copolymer, acrylamides/DMAPA acrylates/methoxy PEG methacrylate copolymer, acrylamidopropyltrimonium chloride/acrylamide copolymer, acrylamidopropyltrimonium chloride/acrylates copolymer, acrylates/acetoacetoxyethyl methacrylate copolymer, acrylates/acrylamide copolymer, acrylates/ammonium methacrylate opolymer, acrylates/t-butylacrylamide copolymer, acrylates/C1-2 succinates/hydroxyacrylates copolymer, acrylates/lauryl acrylate/stearyl acrylate/ethylamine oxide methacrylate copolymer, acrylates/octylacrylamide copolymer, acrylates/octylacrylamide/diphenyl amodimethicone copolymer, acrylates/stearyl acrylate/ethylamine oxide methacrylate copolymer, acrylates/VA copolymer, Acrylates/VP copolymer, Adipic Acid/Diethylenetriamine copolymer, Adipic Acid/dimethylaminohydroxypropyl Diethylenetriamine copolymer, Adipic Acid/epoxypropyl Diethylenetriamine copolymer, Adipic Acid/Isophthalic Acid/neopentyl glycol/Trimethylolpropane copolymer, allyl stearate/VA copolymer, Aminoethylacrylate phosphates/acrylates copolymer, Aminoethylpropanediol-Acrylates/Acrylamide copolymer, Aminoethylpropanediol-AMPD-Acrylates/Diacetoneacrylamide copolymer, ammonium VA/acrylates copolymer, AMPD-Acrylates/Diacetoneacrylamide copolymer, AMP-Acrylates/allyl Methacrylate copolymer, AMP acrylates/C1-18 alkyl Acrylates/C1-8 alkyl acrylamide copolymer, AMP acrylates/diacetoneacrylamide copolymer, AMP-acrylates/dimethylaminoethyl copolymer, *Bacillus*/Rice Bran Extract/Soybean Extract ferment filtrates, bis-Butyloxyamodimethicone/PEG-60 copolymer, butyl acrylate/ethylhexyl methacrylate copolymer, butyl acrylate/hydroxypropyl dimethicone acrylates copolymer, Butylated PVP, butyl ester of Ethylene/MA copolymer, butyl ester of PVM/MA copolymer, calcium/sodium PVM/MA copolymer, Corn Starch/Acrylamide/Sodium acrylate copolymer, Diethylene Glycolamine/Epichlorohydrine/Piperazine Copolymer, Dimethicone Crosspolymer, Diphenyl amodimethicone, ethyl ester of PVM/MA copolymer, Hydrolyzed Wheat Protein/PVP Crosspolymer, isobutylene/ethylmaleimide/Hydroxyethylmaleimide copolymer, isobutylene/MA copolymer, Isobutylmethacrylate/bis-hydroxypropyl dimethicone acrylate copolymer, isopropyl ester of PVM/MA copolymer, Lauryl acrylate Crosspolymer, Lauryl Methacrylate/Glycol dimethacrylate Crosspolymer, MEA sulfites, Methacrylic Acid/Sodium acrylamidomethyl Propane sulfonates copolymer, methacryloyl ethyl betaine/acrylates copolymer, Octylacrylamide/Acrylates/Butylaminoethyl Methacrylate Copolymer, PEG/PPG-25/25 Dimethicone/Acrylates Copolymer, PEG-8/SMDI copolymer, polyacrylamide, polyacrylate-6, Polybeta-Alanine/Glutaric Acid Crosspolymer, Polybutylene Terephthalate, polyester-1, Polyethylacrylate, Polyethylene terephthalate, Polymethacryloyl ethyl betaine, Polypentaerythrityl terephthalate, Polyperfluoroperhydrophenanthrene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium 11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-45, Polyquaternium-46, Polyquaternium-47, Polyquaternium-48, Polyquaternium-49, Polyquaternium-50, Polyquaternium-55, Polyquaternium-56, Polysilicone-9, Polyurethane-1, Polyurethane-6, polyurethane-10, polyvinyl acetate, polyvinyl butyral, polyvinylcaprolactam, polyvinylformamide, polyvinyl imidazolinium acetate, polyvinyl methyl ether, Potassium butyl ester of PVM/MA copolymer, Potassium ethyl ester of PVM/MA copolymer, PPG-70 polyglyceryl-10 ether, PPG-12/SMDI copolymer, PPG-51/SMDI copolymer, PPG-10 sorbitol, PVM/MA copolymer, PVP, PVP/VA/Itaconic Acid copolymer, PVP/VA/vinyl Propionate copolymer, Rhizobian Gum, Rosin acrylate, Shellac, Sodium butyl ester of PVM/MA copolymer, Sodium ethyl ester of PVM/MA copolymer, Sodium Polyacrylate, *Sterculia urens* gum, Terephthalic Acid/Isophthalic Acid/Sodium Isophthalic Acid sulfonate/glycol copolymer, Trimethylolpropane triacrylate trimethylsiloxysilylcarbamoyl pullulan, VA/Crotonates copolymer, VA/Crotonates/Methacryloxybenzophenone-1 copolymer, VA/Crotonates/Vinyl Neodecanoate copolymer, VA/Crotonates/Vinyl Propionate Copolymer, VA/DBM copolymer, VA/Vinyl Butyl Benzoate/Crotonates Copolymer, vinyl amine/vinyl alcohol copolymer, vinyl caprolactam/VP/dimethylaminoethyl methacrylate copolymer, VP/acrylates/lauryl Methacrylate copolymer, VP/dimethylaminoethyl copolymer, VP/DMAPA Acrylates copolymer, VP/Hexadecene copolymer, VP/VA copolymer, VP/vinylcaprolactam/DMAPA acrylates copolymer, Yeast Palmitate and Styrene/VP copolymer.

Examples of nonionic polymers are:
Vinylpyrrolidone/vinyl ester copolymers (BASF) such as those sold under the trademark Luviskol VA 64 and Luviskol VA 73, each vinylpyrrolidone/vinyl acetate copolymers, are preferred nonionic polymers.
Cellulose ethers such as hydroxypropyl cellulose, hydroxyethyl cellulose and methylhydroxypropyl cellulose, as sold for example under the trademarks Culminal and Benecel (AQUALON).
Shellac.
Polyvinylpyrrolidones (BASF) such as those marketed under the name Luviskol.
Siloxanes. These siloxanes may be either water-soluble or water-insoluble. Both volatile and non-volatile siloxanes are suitable, wherein non-volatile siloxanes are understood to be compounds whose boiling point at atmospheric pressure is above 200° C. Preferred siloxanes are polydialkyl siloxanes, such as polydimethylsiloxane, polyalkylaryl siloxanes such as polyphenylmethyl siloxane, ethoxylated polydialkyl siloxanes, and polydialkyl siloxanes which contain amine and/or hydroxyl groups.
Glycoside-substituted silicones.

The further component with gelling function homopolyacrylic acid (INCI: Carbomer), available commercially in various versions under the trade name Carbopol® is preferred. The carbomer is preferably present in a proportion of from about 0.02 to about 3 wt %, preferably from about 0.05 to about 1.5 wt % and more preferably from about 0.2 to about 0.8 wt % relative to the total weight of the cosmetic composition.

The polyvinylpyrrolidones (INCI name: PVP) and vinylpyrrolidone/vinyl acetate copolymers (INCI name VP/VA copolymer) are particularly preferred for use as film-forming polymers as contemplated herein because of their cosmetic effect in combination with the copolymers a) and b), wherein the proportion by weight of these polymers is preferably restricted to quantities between about 1.0 and about 10 wt %. Particularly preferred cosmetic compositions are therefore exemplified in that they further contain from about 1.0 to about 10 wt % polyvinylpyrrolidone and/or vinylpyrrolidone/vinyl acetate copolymer relative to their total weight, most preferably polyvinylpyrrolidone. Particularly preferred cosmetic compositions have a content by weight of polyvinylpyrrolidone and/or vinylpyrrolidone/vinyl acetate copolymer c) from about 2.0 to about 8.5 wt %, preferably from about 3.0 to about 7.0 wt % of the total weight of the cosmetic agent.

The cosmetic composition may comprise other conventional materials of styling products. In particular, additional care products may be considered suitable as further excipients and additives.

The product may contain for example, at least one protein hydrolysate and/or one of its derivatives as a care substance. Protein hydrolysates are product mixtures obtained by acid-, basic- or enzyme-catalyzed decomposition of proteins (albumins). The term protein hydrolysates is understood as contemplated herein to include total hydrolysates as well as individual amino acids and their derivatives and mixtures of various amino acids. The molecular weight of the protein hydrolysates that are usable as contemplated herein is between about 75, the molecular weight of glycine, and about 200,000, the molecular weight preferably has a value from about 75 to about 50,000 and very particularly preferably from about 75 to about 20,000 Daltons.

The composition as contemplated herein may further comprise for example at least one vitamin, one provitamin, one vitamin precursor and/or one of their derivatives as a care substance. In this context, those vitamins, provitamins and vitamin precursors are preferred as contemplated herein that are commonly assigned to the groups A, B, C, E, F and H.

Like the addition of glycerol and/or propylene glycol, the addition of panthenol increases the flexibility of the polymer film which is formed when the product as contemplated herein is used.

The products as contemplated herein may further comprise at least one plant extract, and also mono- or oligosaccharides and/or lipids as a care substance.

Also suitable as a care substance are conditioner oils. The natural and synthetic cosmetic conditioner oils include, for example, vegetable oils, liquid paraffin oils, isoparaffin oils and synthetic hydrocarbons and di-n-alkyl ethers containing a total of 12 to 36 carbon atoms, particularly 12 to 24 carbon atoms. Preferred cosmetic products as contemplated herein contain at least one oil component, preferably at least one oil component selected from the group of silicone oils.

The group of silicone oils includes in particular dimethicone, with which the cyclomethicones are also classified, the amino-functional silicones and dimethiconols. The dimethicones may be either linear or branched, cyclic or cyclic and branched. Suitable silicone oils or silicone gums are particularly dialkyl and alkylaryl siloxanes such as dimethyl polysiloxane and methylphenyl polysiloxane as well as alkoxylated, quaternised or anionic derivatives thereof. Preferred are cyclic and linear polydialkyl siloxanes, alkoxylated and/or aminated derivatives thereof, dihydroxypolydimethyl siloxanes and polyphenylalkyl siloxanes.

Ester oils, i.e. esters of 6-C30-fatty acids with C2-C30 fatty alcohols, preferably monoesters of fatty acids with alcohols having 2 to 24 carbon atoms such as isopropyl myristate (Rilanit® IPM), isononanoic acid C16-18 alkyl ester (Cetiol® SN), 2-ethylhexyl palmitate (Cegesoft® 24), stearic acid-2-ethylhexyl ester (Cetiol® 868), cetyl oleate, glycerol tricaprylate, coconut oil alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristyl (Cetiol® MM), cetearyl isononanoate (Cetiol® SN) oleic acid decyl ester (Cetiol® V) are further preferred care oils.

Dicarboxylic acid esters, symmetrical, asymmetrical or cyclic esters of carbonic acid with fatty alcohols, trifatty acid esters of saturated and/or unsaturated linear and/or branched fatty acids with glycerol or fatty acid partial glycerides including monoglycerides, diglycerides and technical mixtures thereof are also to be considered suitable care substances.

Emulsifiers or surfactants are preferably also contained in the composition as contemplated herein. PEG derivatives of hydrogenated castor oil which are available for example under the name PEG hydrogenated castor oil, such as PEG-30 Hydrogenated Castor Oil, PEG-33 Hydrogenated Castor Oil, PEG-35 Hydrogenated Castor Oil, PEG-36 Hydrogenated Castor Oil or PEG-40 Hydrogenated Castor Oil for example are preferred. The use of PEG-40 Hydrogenated Castor Oil is preferred as contemplated herein. These are preferably present in a quantity from about 0.05 to about 1.5 wt % more preferably from about 0.1 to about 1.0 wt %, also preferably from about 0.2 to about 0.8 wt % or from about 0.3 to about 0.6 wt %.

The cosmetic compositions contain the ingredients and active agents in a cosmetically acceptable carrier.

Preferred cosmetically acceptable carriers are aqueous, alcoholic or aqueous-alcoholic media preferably containing at least about 10 wt % water, calculated on the total weight of the composition.

The cosmetic carrier particularly preferably contains water, particularly in such a quantity that the cosmetic agent contains at least about 10 wt %, particularly at least about 20.0 wt %, most preferably at least about 40 wt % water calculated on the total weight of the composition. Very particularly preferred cosmetic compositions have a water content between about 50 and about 95 wt %, preferably between about 60 and about 90 wt % and particularly between about 65 and about 85 wt % relative to the total weight thereof.

The lower alcohols usually used for cosmetic purposes containing 1 to 4 carbon atoms such as ethanol and isopropanol may be included in particular as alcohols.

Examples of water soluble solvents as cosolvent are glycerol and/or ethylene glycol and/or 1,2-propylene glycol in a quantity from 0 to about 30 wt % relative to the total product.

Table Overview

The composition of some preferred cosmetic products is represented in the following tables (values in wt % relative to the total weight of the cosmetic composition unless otherwise indicated).

|  | Formula 1 | Formula 2 | Formula 3 | Formula 4 | Formula 5 |
| --- | --- | --- | --- | --- | --- |
| Copolymer a) | 1.0 to 5.0 | 1.5 to 4.0 | 1.5 to 4.0 | 2.0 to 3.0 | 2.0 to 3.0 |
| Copolymer b) | 0.1 to 5.0 | 0.1 to 5.0 | 1.0 to 4.0 | 1.0 to 4.0 | 1.5 to 3.0 |
| Misc | to 100 | to 100 | to 100 | to 100 | to 100 |

|  | Formula 1a | Formula 2a | Formula 3a | Formula 4a | Formula 5a |
| --- | --- | --- | --- | --- | --- |
| Copolymer a) | 1.0 to 5.0 | 1.5 to 4.0 | 1.5 to 4.0 | 2.0 to 3.0 | 2.0 to 3.0 |
| Copolymer b) | 0.1 to 5.0 | 0.1 to 5.0 | 1.0 to 4.0 | 1.0 to 4.0 | 1.5 to 3.0 |
| Misc | to 100 | to 100 | to 100 | to 100 | to 100 |

|  | Formula 1b | Formula 2b | Formula 3b | Formula 4b | Formula 5b |
| --- | --- | --- | --- | --- | --- |
| Copolymer a) Gafquat® HS 100 (Values as solid content) | 1.0 to 5.0 | 1.5 to 4.0 | 1.5 to 4.0 | 2.0 to 3.0 | 2.0 to 3.0 |
| Copolymer b) AquaStyle® SH-100 (Values as solid content) | 0.1 to 5.0 | 0.1 to 5.0 | 1.0 to 4.0 | 1.0 to 4.0 | 1.5 to 3.0 |
| Misc | to 100 | to 100 | to 100 | to 100 | to 100 |

|  | Formula 6 | Formula 7 | Formula 8 | Formula 9 | Formula 10 |
| --- | --- | --- | --- | --- | --- |
| Copolymer a) | 1.0 to 5.0 | 1.5 to 4.0 | 1.5 to 4.0 | 2.0 to 3.0 | 2.0 to 3.0 |
| Copolymer b) | 0.1 to 5.0 | 0.1 to 5.0 | 1.0 to 4.0 | 1.0 to 4.0 | 1.5 to 3.0 |

-continued

| | | | | | |
|---|---|---|---|---|---|
| Polyvinyl-pyrrolidone | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

| | Formula 6a | Formula 7a | Formula 8a | Formula 9a | Formula 10a |
|---|---|---|---|---|---|
| Copolymer a) Polyquaternium-28 | 1.0 to 5.0 | 1.5 to 4.0 | 1.5 to 4.0 | 2.0 to 3.0 | 2.0 to 3.0 |
| Copolymer b) Acrylates Copolymer (and) Water | 0.1 to 5.0 | 0.1 to 5.0 | 1.0 to 4.0 | 1.0 to 4.0 | 1.5 to 3.0 |
| Polyvinyl-pyrrolidone | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

| | Formula 6b | Formula 7b | Formula 8b | Formula 9b | Formula 10b |
|---|---|---|---|---|---|
| Copolymer a) Gafquat ® HS 100 (Values as solid content) | 1.0 to 5.0 | 1.5 to 4.0 | 1.5 to 4.0 | 2.0 to 3.0 | 2.0 to 3.0 |
| Copolymer b) AquaStyle ® SH-100 (Values as solid content) | 0.1 to 5.0 | 0.1 to 5.0 | 1.0 to 4.0 | 1.0 to 4.0 | 1.5 to 3.0 |
| Polyvinyl-pyrrolidone | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

| | Formula 11 | Formula 12 | Formula 13 | Formula 14 | Formula 15 |
|---|---|---|---|---|---|
| Copolymer a) | 1.0 to 5.0 | 1.5 to 4.0 | 1.5 to 4.0 | 2.0 to 3.0 | 2.0 to 3.0 |
| Copolymer b) | 0.1 to 5.0 | 0.1 to 5.0 | 1.0 to 4.0 | 1.0 to 4.0 | 1.5 to 3.0 |
| Vinyl-pyrrolidone/ Vinylacetate copolymer | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

| | Formula 11a | Formula 12a | Formula 13a | Formula 14a | Formula 15a |
|---|---|---|---|---|---|
| Copolymer a) Polyquaternium-28 | 1.0 to 5.0 | 1.5 to 4.0 | 1.5 to 4.0 | 2.0 to 3.0 | 2.0 to 3.0 |
| Copolymer b) Acrylates Copolymer (and) Water | 0.1 to 5.0 | 0.1 to 5.0 | 1.0 to 4.0 | 1.0 to 4.0 | 1.5 to 3.0 |
| Vinyl-pyrrolidone/ Vinylacetate copolymer | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

| | Formula 11b | Formula 12b | Formula 13b | Formula 14b | Formula 15b |
|---|---|---|---|---|---|
| Copolymer a) Gafquat ® HS 100 (Values as solid content) | 1.0 to 5.0 | 1.5 to 4.0 | 1.5 to 4.0 | 2.0 to 3.0 | 2.0 to 3.0 |
| Copolymer b) AquaStyle ® SH-100 (Values as solid content) | 0.1 to 5.0 | 0.1 to 5.0 | 1.0 to 4.0 | 1.0 to 4.0 | 1.5 to 3.0 |
| Vinyl-pyrrolidone/ Vinylacetate copolymer | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

-continued

|  | Formula 16 | Formula 17 | Formula 18 | Formula 19 | Formula 20 |
|---|---|---|---|---|---|
| Copolymer a) | 1.0 to 5.0 | 1.5 to 4.0 | 1.5 to 4.0 | 2.0 to 3.0 | 2.0 to 3.0 |
| Copolymer b) | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Misc | to 100 | to 100 | to 100 | to 100 | to 100 |

|  | Formula 16a | Formula 17a | Formula 18a | Formula 19a | Formula 20a |
|---|---|---|---|---|---|
| Copolymer a) Polyquaternium-28 | 1.0 to 5.0 | 1.5 to 4.0 | 1.5 to 4.0 | 2.0 to 3.0 | 2.0 to 3.0 |
| Copolymer b) Acrylates Copolymer (and) Water | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Misc | to 100 | to 100 | to 100 | to 100 | to 100 |

|  | Formula 16b | Formula 17b | Formula 18b | Formula 19b | Formula 20b |
|---|---|---|---|---|---|
| Copolymer a) Gafquat ® HS 100 (Values as solid content) | 1.0 to 5.0 | 1.5 to 4.0 | 1.5 to 4.0 | 2.0 to 3.0 | 2.0 to 3.0 |
| Copolymer b) AquaStyle ® SH-100 (Values as solid content) | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Misc | to 100 | to 100 | to 100 | to 100 | to 100 |

|  | Formula 21 | Formula 22 | Formula 23 | Formula 24 | Formula 25 |
|---|---|---|---|---|---|
| Copolymer a) | 1.0 to 5.0 | 1.5 to 4.0 | 1.5 to 4.0 | 2.0 to 3.0 | 2.0 to 3.0 |
| Copolymer b) | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Misc | to 100 | to 100 | to 100 | to 100 | to 100 |

|  | Formula 21a | Formula 22a | Formula 23a | Formula 24a | Formula 25a |
|---|---|---|---|---|---|
| Copolymer a) Polyquaternium-28 | 1.0 to 5.0 | 1.5 to 4.0 | 1.5 to 4.0 | 2.0 to 3.0 | 2.0 to 3.0 |
| Copolymer b) Acrylates Copolymer (and) Water | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Misc | to 100 | to 100 | to 100 | to 100 | to 100 |

|  | Formula 21b | Formula 22b | Formula 23b | Formula 24b | Formula 25b |
|---|---|---|---|---|---|
| Copolymer a) Gafquat ® HS 100 (Values as solid content) | 1.0 to 5.0 | 1.5 to 4.0 | 1.5 to 4.0 | 2.0 to 3.0 | 2.0 to 3.0 |
| Copolymer b) AquaStyle ® SH-100 (Values as solid content) | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Misc | to 100 | to 100 | to 100 | to 100 | to 100 |

-continued

|  | Formula 26 | Formula 27 | Formula 28 | Formula 29 | Formula 30 |
| --- | --- | --- | --- | --- | --- |
| Copolymer a) | 1.0 to 5.0 | 1.5 to 4.0 | 1.5 to 4.0 | 2.0 to 3.0 | 2.0 to 3.0 |
| Copolymer b) | 0.1 to 5.0 | 0.1 to 5.0 | 1.0 to 4.0 | 1.0 to 4.0 | 1.5 to 3.0 |
| Water | 50 to 95 | 50 to 95 | 60 to 90 | 60 to 90 | 65 to 85 |
| Misc | to 100 | to 100 | to 100 | to 100 | to 100 |

|  | Formula 26a | Formula 27a | Formula 28a | Formula 29a | Formula 30a |
| --- | --- | --- | --- | --- | --- |
| Copolymer a) Polyquaternium-28 | 1.0 to 5.0 | 1.5 to 4.0 | 1.5 to 4.0 | 2.0 to 3.0 | 2.0 to 3.0 |
| Copolymer b) Acrylates Copolymer (and) Water | 0.1 to 5.0 | 0.1 to 5.0 | 1.0 to 4.0 | 1.0 to 4.0 | 1.5 to 3.0 |
| Water | 50 to 95 | 50 to 95 | 60 to 90 | 60 to 90 | 65 to 85 |
| Misc | to 100 | to 100 | to 100 | to 100 | to 100 |

|  | Formula 26b | Formula 27b | Formula 28b | Formula 29b | Formula 30b |
| --- | --- | --- | --- | --- | --- |
| Copolymer a) Gafquat ® HS 100 (Values as solid content) | 1.0 to 5.0 | 1.5 to 4.0 | 1.5 to 4.0 | 2.0 to 3.0 | 2.0 to 3.0 |
| Copolymer b) AquaStyle ® SH-100 (Values as solid content) | 0.1 to 5.0 | 0.1 to 5.0 | 1.0 to 4.0 | 1.0 to 4.0 | 1.5 to 3.0 |
| Water | 50 to 95 | 50 to 95 | 60 to 90 | 60 to 90 | 65 to 85 |
| Misc | to 100 | to 100 | to 100 | to 100 | to 100 |

|  | Formula 31 | Formula 32 | Formula 33 | Formula 34 | Formula 35 |
| --- | --- | --- | --- | --- | --- |
| Copolymer a) | 1.0 to 5.0 | 1.5 to 4.0 | 1.5 to 4.0 | 2.0 to 3.0 | 2.0 to 3.0 |
| Copolymer b) | 0.1 to 5.0 | 0.1 to 5.0 | 1.0 to 4.0 | 1.0 to 4.0 | 1.5 to 3.0 |
| Polyvinyl-pyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 31a | Formula 32a | Formula 33a | Formula 34a | Formula 35a |
| --- | --- | --- | --- | --- | --- |
| Copolymer a) Polyquaternium-28 | 1.0 to 5.0 | 1.5 to 4.0 | 1.5 to 4.0 | 2.0 to 3.0 | 2.0 to 3.0 |
| Copolymer b) Acrylates Copolymer (and) Water | 0.1 to 5.0 | 0.1 to 5.0 | 1.0 to 4.0 | 1.0 to 4.0 | 1.5 to 3.0 |
| Polyvinyl-pyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 31b | Formula 32b | Formula 33b | Formula 34b | Formula 35b |
| --- | --- | --- | --- | --- | --- |
| Copolymer a) Gafquat ® HS 100 (Values as solid content) | 1.0 to 5.0 | 1.5 to 4.0 | 1.5 to 4.0 | 2.0 to 3.0 | 2.0 to 3.0 |
| Copolymer b) AquaStyle ® SH-100 (Values as solid content) | 0.1 to 5.0 | 0.1 to 5.0 | 1.0 to 4.0 | 1.0 to 4.0 | 1.5 to 3.0 |
| Polyvinyl-pyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

-continued

|  | Formula 36 | Formula 37 | Formula 38 | Formula 39 | Formula 40 |
|---|---|---|---|---|---|
| Copolymer a) | 1.0 to 5.0 | 1.5 to 4.0 | 1.5 to 4.0 | 2.0 to 3.0 | 2.0 to 3.0 |
| Copolymer b) | 0.1 to 5.0 | 0.1 to 5.0 | 1.0 to 4.0 | 1.0 to 4.0 | 1.5 to 3.0 |
| Vinyl-pyrrolidone/Vinylacetate copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 36a | Formula 37a | Formula 38a | Formula 39a | Formula 40a |
|---|---|---|---|---|---|
| Copolymer a) Polyquaternium-28 | 1.0 to 5.0 | 1.5 to 4.0 | 1.5 to 4.0 | 2.0 to 3.0 | 2.0 to 3.0 |
| Copolymer b) Acrylates Copolymer (and) Water | 0.1 to 5.0 | 0.1 to 5.0 | 1.0 to 4.0 | 1.0 to 4.0 | 1.5 to 3.0 |
| Vinyl-pyrrolidone/Vinylacetate copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 36b | Formula 37b | Formula 38b | Formula 39b | Formula 40b |
|---|---|---|---|---|---|
| Copolymer a) Gafquat ® HS 100 (Values as solid content) | 1.0 to 5.0 | 1.5 to 4.0 | 1.5 to 4.0 | 2.0 to 3.0 | 2.0 to 3.0 |
| Copolymer b) AquaStyle ® SH-100 (Values as solid content) | 0.1 to 5.0 | 0.1 to 5.0 | 1.0 to 4.0 | 1.0 to 4.0 | 1.5 to 3.0 |
| Vinyl-pyrrolidone/Vinylacetate copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 41 | Formula 42 | Formula 43 | Formula 44 | Formula 45 |
|---|---|---|---|---|---|
| Copolymer a) | 1.0 to 5.0 | 1.5 to 4.0 | 1.5 to 4.0 | 2.0 to 3.0 | 2.0 to 3.0 |
| Copolymer b) | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | to 100 | to 100 | to 100 | to 100 | to 100 |

|  | Formula 41a | Formula 42a | Formula 43a | Formula 44a | Formula 45a |
|---|---|---|---|---|---|
| Copolymer a) Polyquaternium-28 | 1.0 to 5.0 | 1.5 to 4.0 | 1.5 to 4.0 | 2.0 to 3.0 | 2.0 to 3.0 |
| Copolymer b) Acrylates Copolymer (and) Water | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | to 100 | to 100 | to 100 | to 100 | to 100 |

|  | Formula 41b | Formula 42b | Formula 43b | Formula 44b | Formula 45b |
|---|---|---|---|---|---|
| Copolymer a) Gafquat ® HS 100 (Values as solid content) | 1.0 to 5.0 | 1.5 to 4.0 | 1.5 to 4.0 | 2.0 to 3.0 | 2.0 to 3.0 |
| Copolymer b) AquaStyle ® SH-100 (Values as solid content) | 0.1 to 5.0 | 0.1 to 5.0 | 1.0 to 4.0 | 1.0 to 4.0 | 1.5 to 3.0 |

-continued

| | | | | | |
|---|---|---|---|---|---|
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | to 100 | to 100 | to 100 | to 100 | to 100 |

| | Formula 46 | Formula 47 | Formula 48 | Formula 49 | Formula 50 |
|---|---|---|---|---|---|
| Copolymer a) | 1.0 to 5.0 | 1.5 to 4.0 | 1.5 to 4.0 | 2.0 to 3.0 | 2.0 to 3.0 |
| Copolymer b) | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | to 100 | to 100 | to 100 | to 100 | to 100 |

| | Formula 46a | Formula 47a | Formula 48a | Formula 49a | Formula 50a |
|---|---|---|---|---|---|
| Copolymer a) Polyquaternium-28 | 1.0 to 5.0 | 1.5 to 4.0 | 1.5 to 4.0 | 2.0 to 3.0 | 2.0 to 3.0 |
| Copolymer b) Acrylates Copolymer (and) Water | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | to 100 | to 100 | to 100 | to 100 | to 100 |

| | Formula 46b | Formula 47b | Formula 48b | Formula 49b | Formula 50b |
|---|---|---|---|---|---|
| Copolymer a) Gafquat® HS 100 (Values as solid content) | 1.0 to 5.0 | 1.5 to 4.0 | 1.5 to 4.0 | 2.0 to 3.0 | 2.0 to 3.0 |
| Copolymer b) AquaStyle® SH-100 (Values as solid content) | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | to 100 | to 100 | to 100 | to 100 | to 100 |

The heading "Misc" as contemplated herein refers to a cosmetic carrier, particularly (if not listed separately) water and optionally other typical ingredients of styling products.

The cosmetic composition as contemplated herein may be formulated in the manner customary for the temporary reshaping of hair, for example as hair gel, hair spray hair mousse or hair wax. Preferably, the product is formulated as a hair gel.

Both hair foams and hairsprays require the presence of propellants. As contemplated herein should, however, it is preferable to use only small quantities of hydrocarbons, or none at all. Propane, propane/butane mixtures and dimethyl ether are particularly suitable propellants as contemplated herein.

The present disclosure also relates to the use of cosmetic compositions as contemplated herein for the temporary reshaping of keratinous fibres, in particular human hair, and a method for the temporary shaping of keratinous fibres, particularly human hair, in which the cosmetic composition is applied to keratinous fibres.

A further object of this disclosure is the use of a cosmetic composition as contemplated herein to improve the moisture resistance of temporarily reshaped keratinous fibres.

EXAMPLES

The following hair gels were prepared:

| Component/raw material | INCI name or chemical name | V1 | V2 | E1 |
|---|---|---|---|---|
| Gafquat® HS-100[1] | Polyquaternium-28 | 25 | — | 12.5 |
| AquaStyle® SH-100[2] | Acrylates Copolymer (and) Water | — | 16.5 | 8.25 |
| AMP-ULTRA PC 2000 | Aminomethyl propanol | 0.4 | 0.3 | 0.3 |
| Water | | 74.6 | 83.2 | 78.95 |
| Total | | 100 | 100 | 100 |

[1] 20 wt % of active substance in water
[2] 30 wt % of active substance in water The quantities indicated in the table are in wt % of the respective raw material relative to the total composition. The polymer content in each of the compositions V1, V2 and E1 was 5.0 wt %.

The moisture resistance of the styling agents obtained thereby was tested on purified Kerling-strands in an HHCR test (High Humidity Curl Retention Test: 6 h) (average determined on each of 5 hair strands):

|      | V1  | V2  | E1  |
| ---- | --- | --- | --- |
| HHCR | 49% | 72% | 91% |

Accordingly, the polymer combination E1 of the invention E1 exhibited a significantly super-additive, synergistic effect in terms of moisture resistance.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic composition for the temporary reshaping of keratinous fibres, consisting of:
    a polymeric quaternary ammonium compound formed only from the following monomer units;
        vinylpyrrolidone in an amount of from about 40 to about 95 mol %, and
        methacrylamidopropyltrimethylammonium chloride;
    an anionic acrylate copolymer (b) which consists only of the following monomer units;
        at least one methacrylic acid unit,
        at least one ethyl acrylate unit, and
        at least one (meth)acrylic acid alkyl ester which is different from the ethyl acrylate unit (b2) and comprises a hydrophobic group as the ester group;
    at least one alkanolamine; and
    water in a percentage from about 50 to about 95 wt % in relation to the total weight of the cosmetic composition.

2. The cosmetic composition according to claim 1, wherein the polymeric quaternary ammonium compound is present in a weight percentage of from about 1.0 to about 5.0 wt % relative to the total weight of the cosmetic composition.

3. The cosmetic composition according to claim 1, wherein the anionic acrylate copolymer (b) is present in a proportion of from about 0.1 to about 5.0 wt % relative to the total weight of the cosmetic composition.

4. The cosmetic composition according to claim 1, wherein the composition is provided in the form of a hair gel, hairspray, hair foam or hair wax.

5. A method for the temporary shaping of keratinous fibres, the method comprising applying the cosmetic composition according to claim 1 to keratinous fibres.

6. The cosmetic composition according to claim 1, wherein the anionic acrylate copolymer (b) has a viscosity from about 60,000 to about 120,000 cps with a solid content of 2 wt % in an aqueous neutralized solution at 25° C.

7. The cosmetic composition according to claim 1, wherein the polymeric quaternary ammonium compound is a copolymer with INCI name Polyquaternium-28.

8. The cosmetic composition according to claim 1, wherein the at least one alkanolamine comprises 2-amino-1-ethanol, 2-amino-2-methyl propanol, 2-amino-2-methyl-propane-1,3-diol, or combinations thereof.

* * * * *